US008191551B2

(12) United States Patent
Skovgard

(10) Patent No.: US 8,191,551 B2
(45) Date of Patent: Jun. 5, 2012

(54) OXYGEN DELIVERY SYSTEM

(76) Inventor: Joan Skovgard, Laramie, WY (US)

(*) Notice: Subject to any disclaimer, the term of this patent is extended or adjusted under 35 U.S.C. 154(b) by 537 days.

(21) Appl. No.: 12/504,755

(22) Filed: Jul. 17, 2009

(65) Prior Publication Data

US 2011/0011401 A1 Jan. 20, 2011

(51) Int. Cl.
A61G 10/00 (2006.01)
A61M 15/00 (2006.01)
A61M 16/00 (2006.01)
A62B 7/00 (2006.01)
A62B 9/00 (2006.01)
A62B 18/00 (2006.01)
A62C 35/00 (2006.01)
B61B 3/00 (2006.01)
B65H 75/34 (2006.01)
B66C 19/00 (2006.01)
E01B 25/22 (2006.01)

(52) U.S. Cl. ......... 128/204.18; 128/200.24; 128/202.12; 212/328; 104/93; 137/355.23

(58) Field of Classification Search ............. 128/200.24, 128/201.27–201.29, 202.11–202.12, 202.27, 128/204.18, 204.21, 204.27, 205.22, 205.26, 128/207.18; 600/21–22; 212/71, 76, 87, 212/90, 94, 328; 104/89–90, 93, 118; 191/12 R, 191/12.2 R, 12.2 A, 12.4; 137/355.2, 355.23–355.24; 248/329, 330.1; A61G 10/00; A61M 15/00, 16/00; A62C 35/00; A62B 7/00, 9/00, 18/00; B61B 3/00; B65H 75/34; B66C 19/00; E01B 25/22
See application file for complete search history.

(56) References Cited

U.S. PATENT DOCUMENTS

| 642,166 | A | * | 1/1900 | Sherman | 128/201.29 |
|---|---|---|---|---|---|
| 2,268,009 | A | | 12/1941 | Babb et al. | |
| 2,413,386 | A | * | 12/1946 | Schulz | 128/201.29 |
| 2,518,072 | A | | 8/1950 | Rushworth | |
| 4,593,688 | A | * | 6/1986 | Payton | 128/200.28 |
| 4,848,330 | A | * | 7/1989 | Cowles | 128/200.24 |
| 5,236,143 | A | | 8/1993 | Dragon | |
| 5,392,808 | A | | 2/1995 | Pierce | |
| 5,975,120 | A | | 11/1999 | Novosel | |
| 6,065,490 | A | | 5/2000 | Falcone, Jr. | |
| 6,224,027 | B1 | * | 5/2001 | Johnson et al. | 248/125.8 |
| 6,588,444 | B2 | | 7/2003 | Paplow et al. | |
| 6,591,858 | B2 | | 7/2003 | Peterson | |
| 6,889,688 | B1 | | 5/2005 | Wright | |
| 2003/0146332 | A1 | | 8/2003 | Vinding | |

OTHER PUBLICATIONS

International Search Report, International Searching Authority, Sep. 7, 2010, pp. 1-11.

* cited by examiner

Primary Examiner — Oren Ginsberg
(74) Attorney, Agent, or Firm — Stephen B. Katsaros; Samuel M. Freund; Cochran Freund & Young LLC

(57) ABSTRACT

Disclosed are apparatus and method for delivering oxygen from an oxygen supply to a person in a convenient, sanitary and organized manner. The oxygen delivery system includes a rail attached to a surface of the room and a sliding trolley attached to the rail. An oxygen supply tube is attached to the oxygen supply and the trolley for transferring oxygen from the oxygen supply to the trolley. The system enables the person to move to various locations in the room while receiving oxygen from the oxygen supply through the oxygen supply tube, the trolley, a drop tube and a nasal cannula, or other breathing device connected to the trolley. The person may guide the trolley around the room by pulling the drop tube in the desired direction of travel.

14 Claims, 6 Drawing Sheets

OXYGEN DELIVERY SYSTEM

BACKGROUND OF THE INVENTION

Oxygen therapy is the artificial increase of oxygen uptake and is used to treat emphysema, pneumonia, some heart disorders, and any disease that impairs the body's ability to take up and use oxygen. Oxygen therapy is used in a hospital, or a patient's home, by using an oxygen mask, or a nasal cannula, connected to an oxygen supply (e.g. an oxygen tank, a portable oxygen generator, or a wall connection in a hospital) via a supply tube. The supply tube connected to the oxygen supply is often long in order to allow the patient to move around the room. The long supply tube is commonly piled on the floor near the oxygen supply in an unorganized manner and vulnerable to contacting undesirable substances found on the floor, such as bacterial containing matter, dirt, dust, debris, etc.

SUMMARY OF THE INVENTION

The present invention may therefore include an oxygen delivery system in a room for delivering oxygen from a supply to a person comprising: a rail attached to a surface of the room, the rail having a first end and a second end; a trolley movably attached to the rail; an oxygen supply tube attached to the supply and to the trolley for transferring the oxygen from the supply to the trolley; a tube accumulator for gathering and dispensing the oxygen supply tube, the tube accumulator located between the supply and the trolley; and a drop tube attached to the trolley for transferring the oxygen from the trolley to the person.

The present invention may further include a method of delivering oxygen from an oxygen supply to a person in a room comprising: providing a rail attached to a surface of the room, the rail defining a first end and a second end; providing a trolley movably attached to the rail; providing an oxygen supply tube attached to the oxygen supply and the trolley; moving the trolley on the rail in response to movement of the person; and delivering the oxygen from the oxygen supply to the person with the oxygen supply tube.

DETAILED DESCRIPTION

Figure 1:
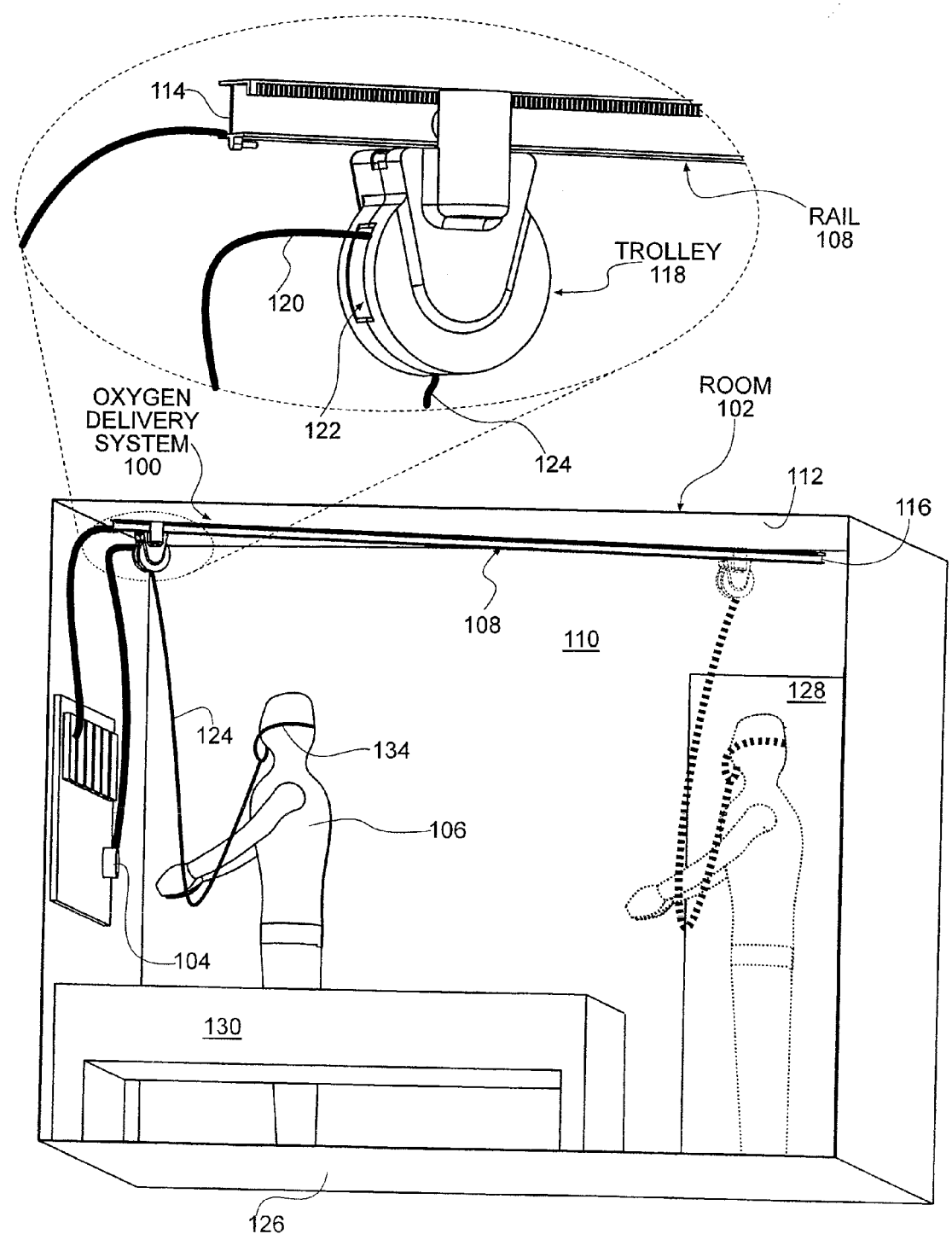
FIG. 1 is a perspective view of one embodiment of an oxygen delivery system in a room for transferring oxygen from an oxygen supply to a person as the person moves within the room, utilizing a trolley that moves along a rail.

Reference will now be made in detail to the present embodiments of the invention. In what follows, identical or similar structure is labeled with identical reference characters.

FIG. 1 is a perspective view of an oxygen delivery system 100 in a room 102 that delivers oxygen from an oxygen supply 104 to a person 106 in a convenient, sanitary and organized manner. The oxygen delivery system 100 includes a rail 108 attached to a surface (for example, a wall 110 or a ceiling 112) of the room 102. The rail 108 has a first end 114 and a second end 116. A trolley 118 is movably attached to the rail 108 and is movable between the ends 114, 116. An oxygen supply tube 120 is attached to the oxygen supply 104 and the trolley 118 for transferring oxygen from the oxygen supply 104 to the trolley 118. The oxygen supply tube 120 may be any of a variety of types of tubing typically used in a medical environment such as, for example, non-toxic polyvinylchloride, 'PVC'. A tube accumulator 122 stores excess amounts of the oxygen supply tube 120 to prevent the oxygen supply tube 120 from touching the floor 126 that may harbor undesirable substances, such as bacterial containing matter, dirt, dust, debris, etc. Although the tube accumulator 122 may be located anywhere along the length of the oxygen supply tube 120, one embodiment has the tube accumulator 122 located inside the trolley 118. Oxygen can flow from the oxygen supply 104, through the oxygen supply tube 120 to the tube accumulator 122. From the tube accumulator 122, the oxygen can travel through a drop tube 124 attached to the trolley 118 to the person 106. Drop tube 124 may terminate with an oxygen mask or, as illustrated, a nasal cannula 134. The present oxygen delivery system 100 enables the person 106 to move to various locations in the room 102 while receiving oxygen from the oxygen supply 104 by directing the trolley 118 using drop tube 124. For example, as illustrated in FIG. 1, the person 106 can move in the room 102 from a location near a bed 130 to a variety of alternate locations, such as by a door 128, with the trolley 118 traveling along the rail 108 as the tube accumulator 122 dispenses the accumulated oxygen supply tube 120. The oxygen delivery system 100 keeps the oxygen supply tube 120 organized and off a floor 126 as oxygen is delivered to the person 106. When the trolley 118 is moved toward the rail first end 114, slack in the oxygen supply tube 120 is collected by the tube accumulator 122 in the trolley 118. Once the person 106 is at a desired position, the drop tube 124 is released and the trolley 118 comes to rest.

Figure 2:
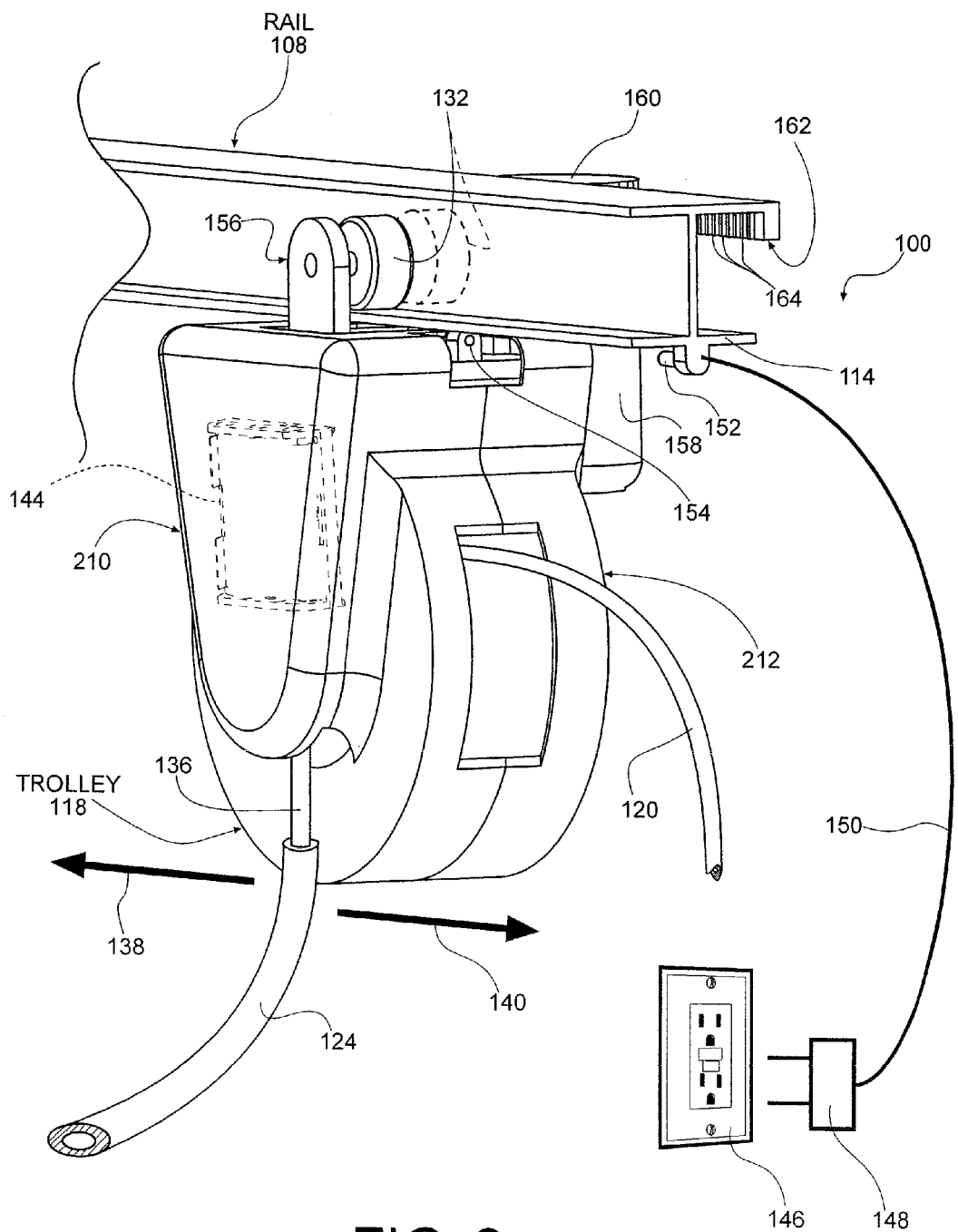
FIG. 2 is a perspective view of the trolley portion of the oxygen delivery system shown in FIG. 1.

FIG. 2 is a perspective view of the oxygen delivery system 100 wherein the trolley 118 may be provided with at least one pair of wheels 132. Wheels 132 are adapted to allow the trolley 118 to slide anywhere between the rail ends 114, 116. The trolley 118 also includes a drop tube connector 136 for receiving the drop tube 124. In one embodiment of the invention, the drop tube 124 is slid over the drop tube connector 136 to provide a firm attachment that is able to withstand the person 106 pulling on the drop tube 124 or oxygen pressure inside the drop tube 124. However, since the drop tube 124 needs to be replaced occasionally, this connection is temporary and the drop tube 124 can be released to enable installation of a new drop tube 124. Use of detachable tube connection devices is also contemplated.

With continued reference to FIG. 2, the trolley 118 may be provided with a battery pack 144 holding replaceable cells (not shown) to power a motor 158 that aids movement of the trolley 118 by engaging a gear 160 with a rack 162. If the trolley 118 is aided by the motor 158 as illustrated, movement of the drop tube 136 in either a forward direction 138 or a backward direction 140 is sensed by switches described below in FIG. 3 and located in the trolley 118. The battery pack 144 can be recharged from an electrical outlet 146 through an electrical path including a plug 148, a power cable 150, a first connector 152, and a second connector 154. The plug 148 is attached to one end of the power cable 150 while the first connector 152 is attached to an opposite end of the power cable 150 and located at the rail first end 114. The second connector 154 may be attached to the trolley 118 and wires (not shown) electrically interface the second connector 154 to the battery pack 144 for recharging when the trolley 118 is docked (for example, when the person 106 is resting on the bed 130) through a battery controller (not shown) that conditions (e.g. voltage control or conversion such as ac-to-dc) and monitors electricity supplied to the battery pack 144. Although a gearing reduction may be required to reduce speed and increase torque from the motor 158, the simple gear 160 is illustrated mounted to a rotating shaft of the motor 158. The gear 160 engages the rack 162 adjoining the rail 108. The toothed rack 162 is made of a plurality of teeth 164 either integrally formed with the rail 108 or, alternatively, a separate component that is attached to the rail 108.

Figure 3:
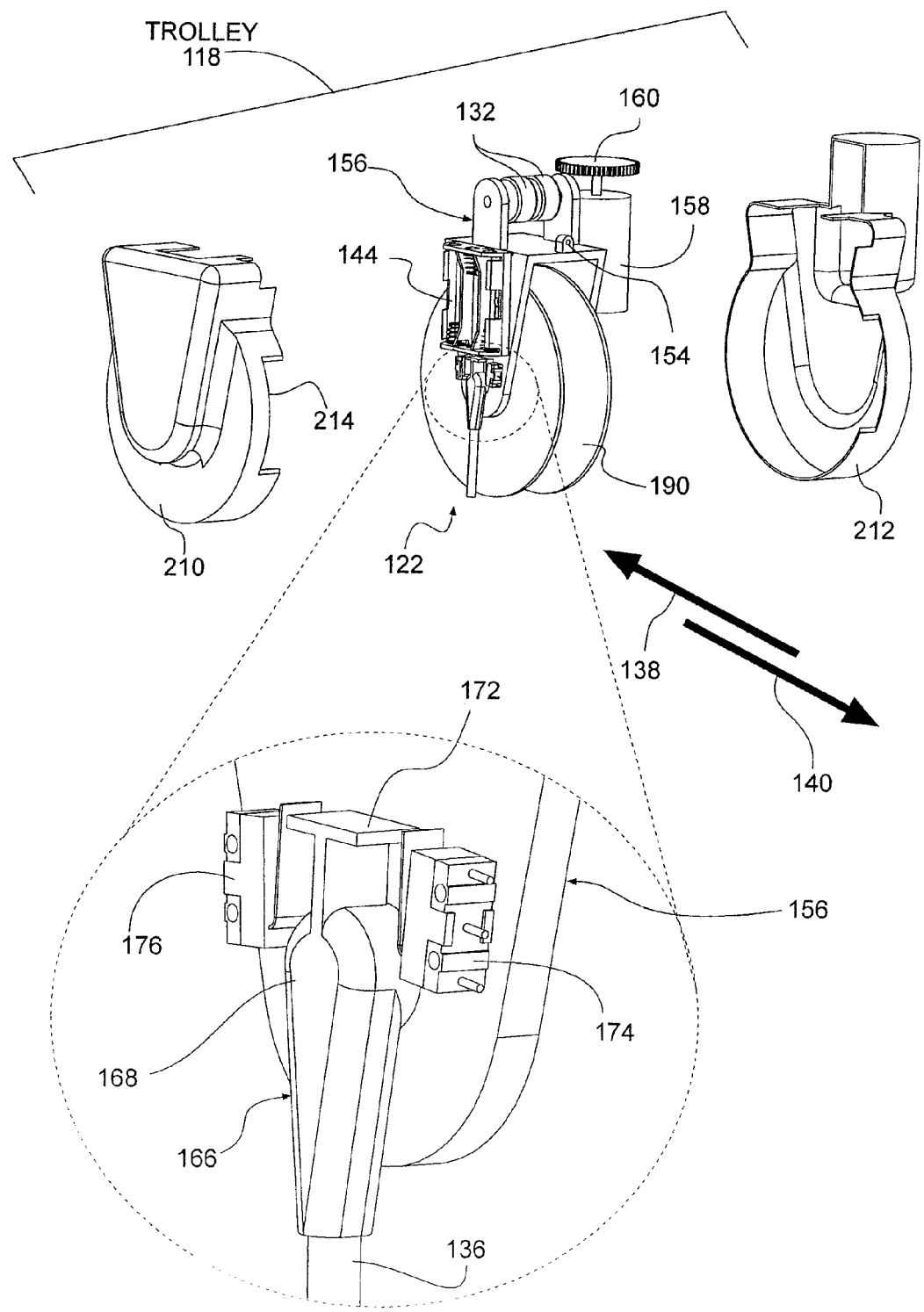
FIG. 3 is an exploded perspective view of the trolley of the oxygen delivery system of FIG. 1 with an enlargement showing an axle and switches responsive to movement of the person.

FIG. 3 is an exploded perspective view of the trolley 118 showing an axle 166 rotatably mounted in the frame 156. The axle 166 may include the drop tube connector 136 formed on the axle first end 168. The axle 166 may also include a tang 172 formed on the axle first end 168. The trolley 118 may also include a forward switch 174 and a backward switch 176. The switches 174 and 176 are attached to the frame 156 in positions where rotation of the axle 166 causes activation of one of the switches 174, 176. For example, if the drop tube 124 is pulled in the forward direction 138, the forward switch 174 is activated by the tang 172. The activated forward switch 174 causes the motor 158 to move trolley 118 in the forward direction 138 to follow movement of the drop tube 124. The switches 174, 176 may reverse polarity of the electricity supplied to the motor 158 or, alternatively, may condition alternating current to cause the shaft of the motor to turn oppositely. The trolley 118 is fully assembled by attaching a left cover 210 and a right cover 212. The covers 210, 212 have a port 214 formed to allow the oxygen supply tube 120 to access the reel 190.

Figure 4:
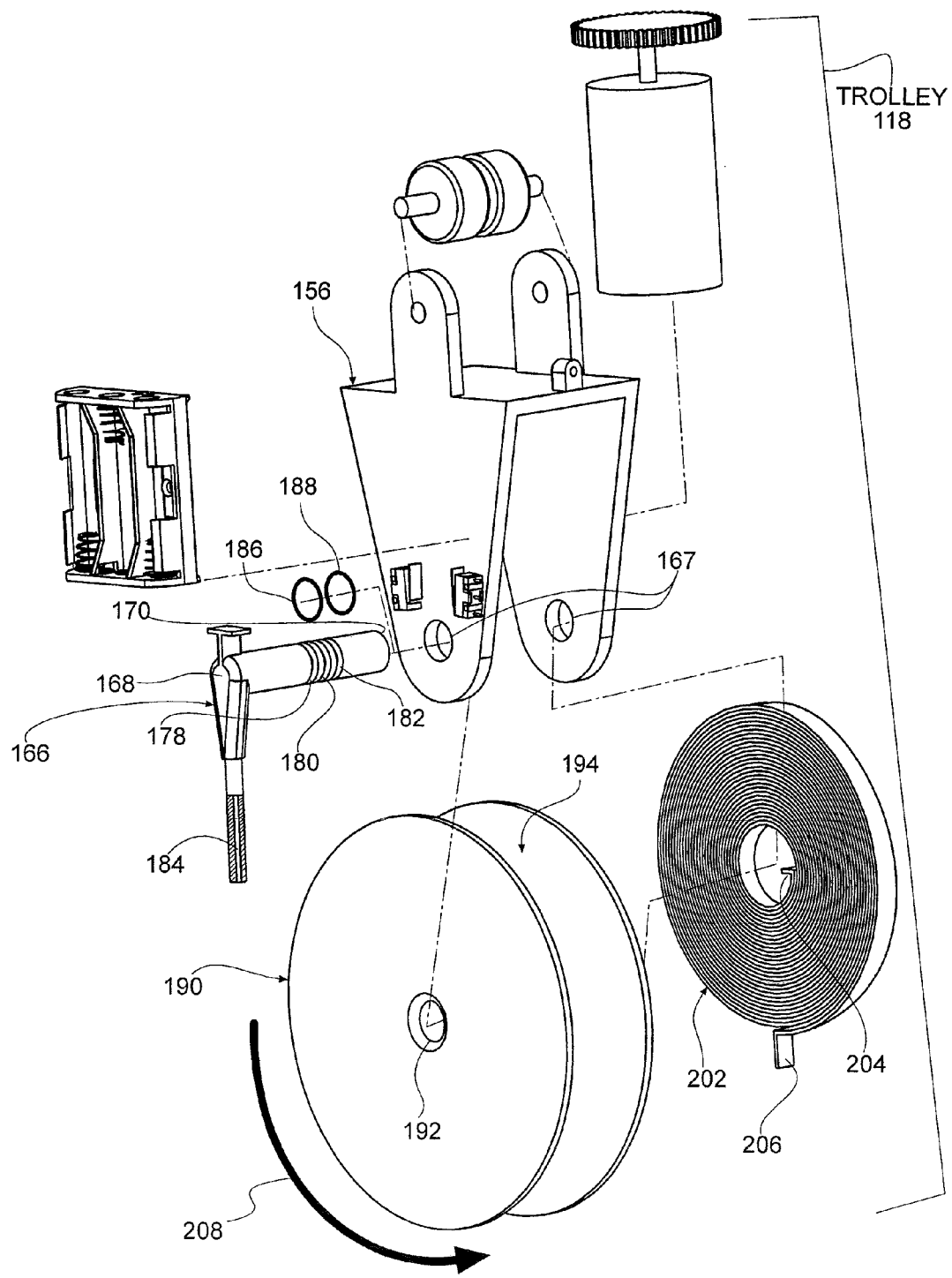
FIG. 4 is an exploded perspective view of interior components of the trolley of FIG. 3 illustrating one exemplary tube accumulator that includes a reel and a spring.

FIG. 4 is an exploded perspective view of interior components (e.g. tube accumulator 122) of the trolley 118 showing the axle 166 having a cylindrical profile that extends between the first end 168 and the second end 170. The axle 166 is provided with a rotary coupler, such as the dual o-ring seal illustrated having a first groove 178, a second groove 180, and a third groove 182 sequentially formed in the cylindrical profile. The axle 166 has an interior tube 184 that begins at the drop tube connector 136 extends through the second groove 180. The tube accumulator 122 may include a spring 202 effective for winding the oxygen supply tube 120 around the reel 190. The spring 202 can be made of a variety of materials (e.g. a flat piece of spring steel) having a first tang 204 and a second tang 206 at the ends of the spring 202. The first tang 204 is affixed to the reel 190 and the second tang 206 is affixed to the frame 156, such that the spring 202 is captured between the reel 190 and the frame 156. The spring 202 is coaxial to the axle 166. This assemblage causes the reel 190 to be tensioned as indicated by arrow 208. The spring 202 creates a recoiling reel 190 that stores the oxygen supply tube 120 on the reel 190 in its coiled condition permitting the return of the oxygen supply tube 120 to the reel 190 when uncoiled.

Figure 5:
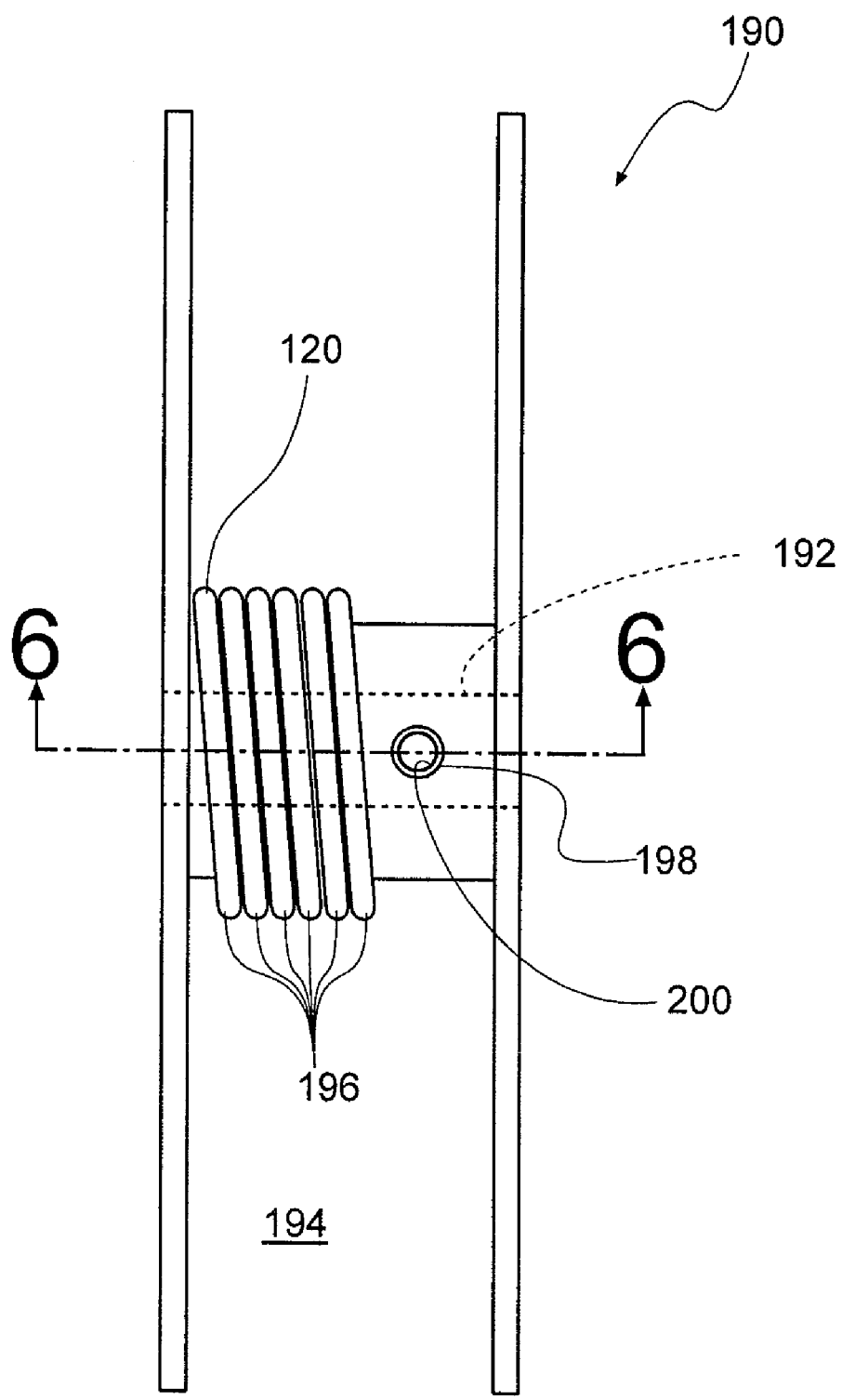
FIG. 5 is a top plan view of the embodiment of the reel illustrated in FIG. 4.

FIG. 5 is a top plan view of the tube accumulator 122 configured with the reel 190 having a bore 192 located at the center of the reel 190. The bore 192 extends through the reel 190 and is adapted to rotationally support the reel 190 when it is mounted on the axle 166. The reel 190 is adapted to receive the oxygen supply tube 120 in a series of circumferential wraps 196 which take up the oxygen supply tube 120 in a controlled manner so that it is organized and readily available when needed. The reel 190 also includes a supply tube connector 198 having a hole 200 formed therein that extends through the supply tube connector 198 to the bore 192.

Figure 6:
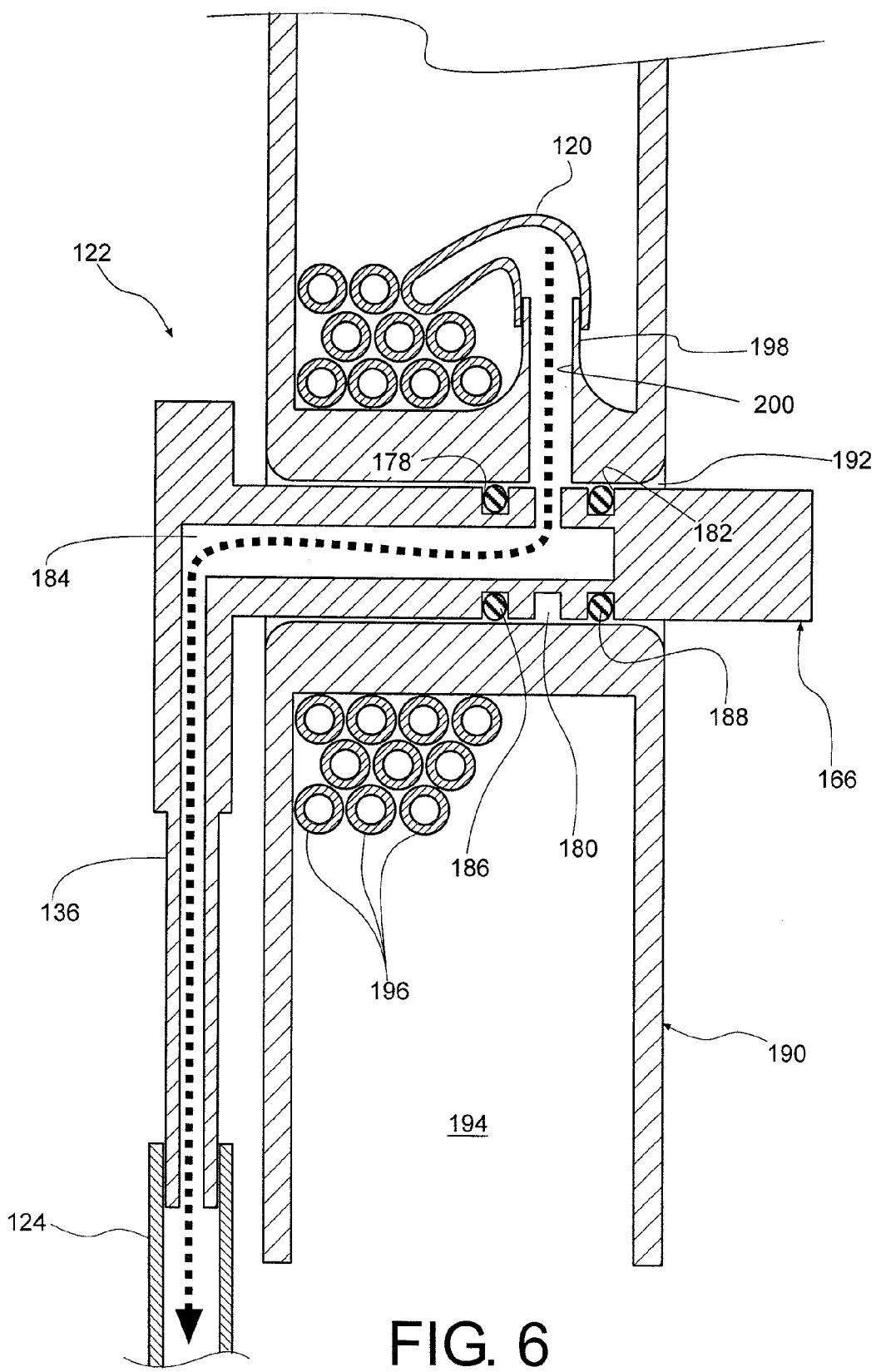
FIG. 6 is a cross-sectional view of the reel of FIG. 5 (taken across plane 6-6 in FIG. 5) showing an embodiment of an axle for providing transfer of oxygen from the rotating reel to the relatively stationary axle.

FIG. 6 is a cross-sectional view of the tube accumulator 122 of FIG. 5 taken across plane 6-6 showing that the reel 190 is located on the axle 166 such that the reel 190 is rotationally supported by the axle 166. The bore 192 receives the axle 166 with the reel supply tube connector hole 200 aligned with the second groove 180. The tube accumulator 122 may include a first o-ring 186 and a second o-ring 188. The first o-ring 186 is located in the first groove 178 and the second o-ring 188 is located in the third groove 182. The o-rings 186, 188 seal against the reel bore 192 to allow a rotational seal between the axle interior tube 184 and the reel supply tube connector hole 200. As illustrated by the dashed line, oxygen can flow between the reel supply tube connector 198 and the axle drop tube connector 136 while the reel 190 rotates about the axle 166 as the circumferential wraps 196 of the oxygen supply tube 120 are formed or unwrapped.

Having described various embodiments of the oxygen delivery system 100, flow of oxygen from the oxygen supply 104 to the person 106 will be traced for illustrative purposes. Starting at the oxygen supply 104, oxygen flows into the oxygen supply tube 120 where it travels towards the ceiling 112. The oxygen supply tube 120 may be guided by a channel or clips (neither shown) to control the position of the oxygen supply tube 120. The oxygen supply tube 120 enters the trolley 118 at the port 214. Once inside the trolley 118, oxygen travels around the reel 190 as it travels through the circumferential wraps 196 of the oxygen supply tube 120. The oxygen enters the interior tube 184 of the axle 166 through tube connector 198. The drop tube 124 is attached to the axle drop tube connector 136, such that oxygen exits the axle interior tube 184 and enters the drop tube 124. Oxygen travels from the drop tube 124 to the nasal cannula 134 where it is introduced to the nasal passages of the person 106. This process can occur independent of the location of the person 106 in the room 102, for example, the location illustrated in phantom line by the door 128.

Having provided a description of flow of oxygen, an exemplary process of installing the oxygen delivery system 100 in the room 102 will be provided. With reference again to FIG. 1, the rail 108 may be provided by a manufacturer with the trolley 118 preinstalled at the time of manufacture. The rail 108, with the installed trolley 118, is attached to the ceiling 112 of the room 102. Although many attachment devices may be used, one attachment method is to anchor the rail 108 to the ceiling 112 with lag bolts (not shown). The attachment may place the rail first end 114 near the oxygen supply 104 to minimize the length of the oxygen supply tube 120 extending from the oxygen supply 104 to the rail first end 114. The rail second end 116 is located in a direction where the person 106 commonly travels. For example, the rail second end 116 is mounted near the door 128, or a bathroom (not shown), so that it extends diagonally across the ceiling 112. After attachment of the rail 108, the power cable 150 is plugged into the electrical outlet 146 via the plug 148. The oxygen supply tube 120 is attached at one end to the oxygen supply 104 while the other end is attached to the supply tube connector 198 of the reel 190. It should be mentioned that the circumferential wraps 196 around the reel 190 are formed in the circumferential pocket 194 between the two ends of the oxygen supply tube 120. Initial installation of the oxygen delivery system 100 continues with attachment of the drop tube 124 to the drop tube connector 136 on the trolley 118. The opposite end of the drop tube 124 is attached to the nasal cannula 134. The exemplary installation process described above places the oxygen delivery system 100 into a condition where it can be used by the person 106 to supply oxygen as the person 106 moves around the room 102.

In one exemplary embodiment, the oxygen delivery system 100 is provided with replaceable oxygen supply and drop tubes 120, 124. In some applications, different users will occupy the room 102. For example, if used in a hospital, a patient may occupy the room for a few days to a few weeks at which time the oxygen supply tube 120 and the drop tube 124 may need to be replaced. To accomplish the replacement, the trolley 118 is moved towards the rail second end 116 so that the entire length of the oxygen supply tube 120 is accessible. The reel 190 is grasped (for example, a pin, not shown) so that return energy stored in the spring 202 is not inadvertently used to spin the reel 190 when the oxygen supply tube 120 is released. After grasping the reel 190, the oxygen supply tube 120 can be released from the supply tube connector 198 of the reel 190. Additionally, the oxygen supply tube 120 is detached from the oxygen supply 104 to entirely release the oxygen supply tube 120 from the oxygen delivery system 100. The released oxygen supply tube 120 is removed from the oxygen delivery system 100 and replaced by a new oxygen supply tube 120. Installation of this new oxygen supply tube 120 is essentially opposite of the process described for releasing the old oxygen supply tube 120. The drop tube 124 is replaced by detaching the old drop tube 124 from the drop tube connector 136 on the trolley 118 and, then, installing a new drop tube 124.

In another exemplary alternative embodiment, the rail 108 may be formed with one or more arcs rather than the straight section illustrated in the FIGURES. This alternative configuration of the rail 108 may be useful for some configurations of the room 102, for example, if the room 102 has an 'L' shape. The rail 108 could have one 90 degree bend at the corner of the 'L' that unions two straight sections to allow the person 106 to move around the entire area of the room 102.

In another exemplary alternative embodiment, the rail 108 may have an intersection (not shown) forming a branch line of the rail 108 to allow for two different paths to be taken. For example, in a traditional hospital room, the person 106 may have two paths for moving around the room: 1) towards the bathroom and 2) towards the window. In this instance, the user may be able to direct the trolley 118 to take one of the two paths at the intersection to allow for uninhibited travel to either the bathroom or the window.

In another exemplary alternative embodiment, the tube accumulator 122 is configured with a second motor (not shown) instead of the spring 202. If provided, the second motor controls the collection and dispensing of the oxygen supply tube 120 by mechanically interfacing with the reel 190 The second motor has a rotor that rotates causing rotation of the reel 190.

The foregoing description of the invention has been presented for purposes of illustration and description. It is not intended to be exhaustive or to limit the invention to the precise form disclosed, and other modifications and variation may be possible in light of the above teachings. The embodiment was chosen and described in order to best explain the principles of the invention and its practical applications to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An oxygen delivery system in a room for delivering oxygen from an oxygen supply to a person comprising:
    a rail attached to a surface of said room, said rail having a first end and a second end;
    a trolley movably attached to said rail;
    an oxygen supply tube attached to said supply and said trolley for transferring said oxygen from said supply to said trolley;
    a tube accumulator for gathering and dispensing said oxygen supply tube, said tube accumulator located between said supply and said trolley;
    a drop tube attached to said trolley for transferring said oxygen from said trolley to said person; a rack attached to said rail, said rack comprising a plurality of teeth; a motor disposed in said trolley and having a rotor; and a gear attached to said rotor adapted to engage with said rack such that rotation of said rotor causes said trolley to move along said rail.

2. The oxygen delivery system of claim 1 wherein said tube accumulator comprises a reel located in said tube accumulator for gathering said oxygen supply tube in a plurality of circumferential wraps.

3. The oxygen delivery system of claim 2 wherein said tube accumulator further comprises a spring for biasing said reel for collecting said oxygen supply tube around said reel into the plurality of circumferential wraps.

4. The oxygen delivery system of claim 2 wherein said tube accumulator further comprises a rotary coupler coaxial to said reel for transferring said oxygen from said oxygen supply tube gathered on said reel to said drop tube.

5. The oxygen delivery system of claim 1 wherein said trolley comprises:
    a rechargeable battery attached to said motor for providing power to said motor;
    a first power connector electrically connected to a battery controller effective for charging said rechargeable battery; and
    a second power connector attached to said rail first end, said second power connector electrically connected to an electrical outlet in said room for transferring electricity from said electrical outlet to said battery controller through said first power connector and said second power connector.

6. The oxygen delivery system of claim 1 wherein said trolley comprises:
    a forward switch responsive to movement of said drop tube; and
    a reverse switch responsive to movement of said drop tube, for causing said trolley to move with said person.

7. The oxygen delivery system of claim 6 wherein said trolley further comprises:
    an axle coaxial to said reel about which said reel rotates;
    a connector formed on one end of said axle for receiving said drop tube; and
    a tang formed on said connector, said tang contacting said forward switch when said drop tube is moved from said trolley towards said rail second end, and said tang contacting said reverse switch when said drop tube is moved from said trolley towards said rail first end.

8. A method of delivering oxygen from an oxygen supply to a person in a room comprising:
    providing a rail attached to a surface of said room, said rail defining a first end and a second end;
    providing a trolley movably attached to said rail;
    providing an oxygen supply tube attached to said oxygen supply and said trolley;

moving said trolley on said rail in response to movement of said person;

delivering said oxygen from said oxygen supply to said person through said oxygen supply tube; providing a rack adjoining said rail, said rack comprising a plurality of teeth; providing a motor disposed in said trolley; and providing a gear attached to said motor, said gear interfaced with said teeth of said rack whereby rotation of said motor causes said trolley to move along said rail between said rail first end and said rail second end.

9. The method of claim 8 further comprising:

providing a tube accumulator for storing said oxygen supply tube, said tube accumulator located between said oxygen supply and said trolley; and accumulating said oxygen supply tube with said tube accumulator as said trolley moves on said rail.

10. The method of claim 9 wherein said step of providing said tube accumulator further comprises:

providing a reel located in said tube accumulator for storing said oxygen supply tube in a plurality of circumferential wraps; and wrapping said oxygen supply tube into said plurality of circumferential wraps around said reel.

11. The method of claim 10 wherein said step of providing said tube accumulator further comprises:

providing a spring interfaced with said reel and said trolley; and biasing said oxygen supply tube around said reel with said spring so that said oxygen tube is formed into said plurality of circumferential wraps.

12. The method of claim 8 further comprising:

providing a motor disposed in said trolley and engaged with said rail;

providing a rechargeable battery disposed in said trolley and electrically connected to said motor;

providing a battery controller effective for charging said rechargeable battery;

providing a first power connector attached to said trolley, said first power connector electrically connected to said rechargeable battery;

providing a second power connector attached to said rail first end and an electrical outlet in said room;

docking said trolley near said rail first end thereby connecting said first power connector to said second power connector; and transferring electricity from said electrical outlet to said battery through said first power connector and said second power connector after said docking.

13. The method of claim 8 and further comprising:

providing a drop tube attached to said trolley;

transferring said oxygen from said trolley to said person while said person is located at various locations in said room while delivering said oxygen from said supply via said oxygen supply tube, said trolley, and said drop tube;

providing a motor disposed in said trolley and engaged with said rail;

providing a forward switch responsive to movement of said drop tube for activating said motor to cause said trolley to move toward said rail second end; and providing a reverse switch responsive to movement of said drop tube for activating said motor to cause said trolley to move toward said rail first end.

14. The method of claim 13 and further comprising:

providing an axle coaxial to said reel about which said reel rotates;

providing a drop tube connector formed on one end of said axle for receiving said drop tube;

providing a tang formed on said axle adjoining said drop tube connector;

contacting said forward switch with said tang when said drop tube is moved towards said rail second end;

contacting said reverse switch with said tang when said drop tube is moved towards said rail first end;

moving said trolley between said rail first end and said rail second end when said forward switch is contacted; and moving said trolley between said rail second end and said rail first end when said reverse switch is contacted.

* * * * *